US00PP08484P

United States Patent [19]

Suzuki

[11] Patent Number: Plant 8,484

[45] Date of Patent: Dec. 7, 1993

[54] ROSE PLANT — KEINOUMI VARIETY

[75] Inventor: Seizo Suzuki, Tokyo, Japan

[73] Assignee: The Conard-Pyle Company, West Grove, Pa.

[21] Appl. No.: 972,544

[22] Filed: Nov. 6, 1992

[51] Int. Cl.[5] ..... A01H 5/00

[52] U.S. Cl. ..... Plt./28

[58] Field of Search ..... Plt./28, 22, 29

[56] References Cited

U.S. PATENT DOCUMENTS

P.P. 4,559 7/1980 Jelly ..... Plt. 28

P.P. 6,669 3/1989 Hoy, Jr. ..... Plt. 28

*Primary Examiner*—Howard J. Locker

*Assistant Examiner*—E. F. McElwain

*Attorney, Agent, or Firm*—Burns, Doane, Swecker & Mathis

[57] ABSTRACT

A new and distinct variety of Polyantha rose plant is provided which abundantly forms attractive semi-double long lasting blossoms which are an attractive bright red coloration. The plant exhibits an upright growth habit and forms vigorous vegetation. Excellent aptitude to forcing in a greenhouse is exhibited and the plant is particularly well suited for spray-type cut flower production. Additionally, the plant exhibits disease resistance.

1 Drawing Sheet

SUMMARY OF THE INVENTION

The new variety of Polyantha rose plant was created by artificial pollination wherein two parents were crossed which previously had been studied in the hope that they would contribute the desired characteristics. The female parent (i.e., the seed parent) of the new variety was an unnamed seedling (nonpatented in the United States). The male parent (i.e., the pollen parent) was the HILTACO variety (U.S. Plant Pat. No. 4,559). The parentage of the new variety can be summarized as follows:

Unnamed Seedling×HILTACO.

The seeds resulting from the above pollination were sown and small plants were obtained which were physically and biologically different from each other. Selective study resulted in the identification of a single plant of the new variety.

It was found that the new variety of Polyantha rose plant of the present invention possesses the following combination of characteristics:

(a) forms in abundance attractive long lasting semi-double bright red blossoms,
(b) exhibits an excellent capacity to be forced in the greenhouse for the production of spray-type fresh flowers,
(c) forms vigorous vegetation,
(d) exhibits an upright growth habit, and
(e) is not particularly affected to cryptogamic diseases.

The new variety well meets the needs of the horticultural industry and is particularly well suited for use in the production of attractive cut flowers sprays. The brilliant coloration of the blossoms holds well in a vase.

The new variety has been found to undergo asexual propagation in Japan, France, and the United States by a number of routes, including budding, grafting, cuttage, etc. The characteristics of the new variety have been found to be strictly transmissible by such asexual propagation from one generation to another.

The new variety of the present invention exhibits good resistance to diseases commonly encountered during the commercial production of cut flowers in the greenhouse, such as powdery mildew and downy mildew. This disease resistance makes possible the production of quality cut flowers in the absence of any significant diminution in quality as the result of such diseases.

The new variety can be readily distinguished from the parent HILTACO variety (U.S. Plant Pat. No. 4,559) and the CHARADE variety (U.S. Plant Pat. No. 6,669). For instance, when compared to the HILTACO variety, the new variety commonly exhibits, inter alia, semi-dull foliage having a more elliptic configuration, smaller thorns, superior resistance to powdery mildew, and the absence of blossom fragrance. When compared to the CHARADE variety, the new variety commonly exhibits, inter alia, darker foliage, smaller thorns, and the absence of blossom fragrance.

The new variety has been named the KEINOUMI variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Cap d' Antibes, France.

FIG. 1 — illustrates a specimens of a young shoot;

FIG. 2 — illustrates specimens of two floral buds before the opening of the sepals;

FIG. 3 — illustrates specimens of two floral buds at the opening of the sepals;

FIG. 4 — illustrates specimens of two floral buds at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch showing the adult wood;

FIG. 14 — illustrates specimens of leaves with three leaflets — plan view — upper surface (top) and lower surface (bottom);

FIG. 15 — illustrates a specimen of a leaf with five leaflets — plan view — under surface; and FIG. 16 — illustrates a specimen of a leaf with seven leaflets — plan view — upper surface.

DETAILED DESCRIPTION

Figures 1, 2, 3, 4, 5, 6, 7, 8, 9, 10, 11, 12, 13, 14, 15, 16:
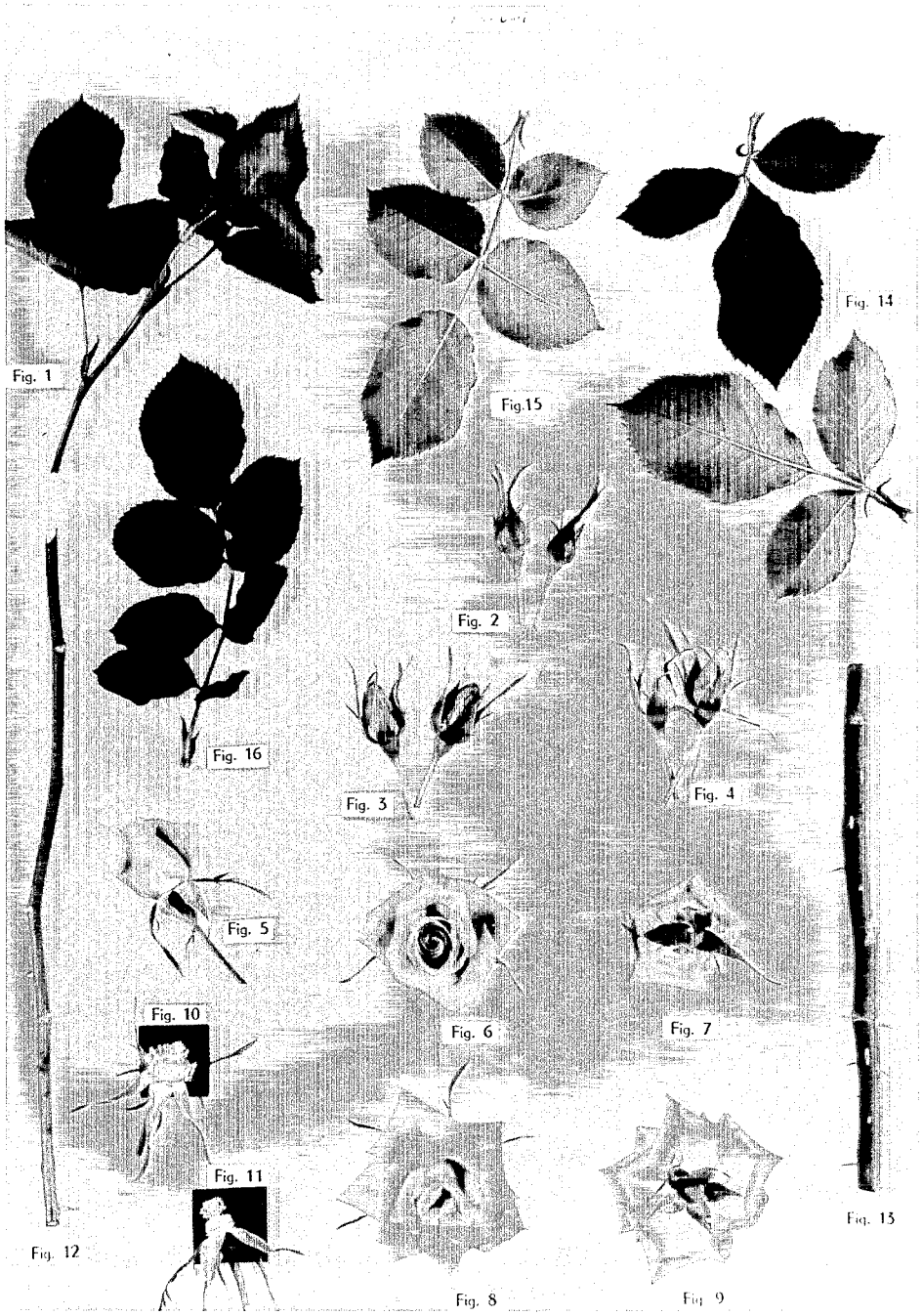

The chart used in the identification of the colors is that of The Royal Horticultural Society (R.H.S. Colour Chart). The description is based on the observation of two year old plants made during November while budded on *Rosa indica* understock and growing in greenhouse at Cap d' Antibes, France. The coloration in common terms precedes reference to the chart.

Class: Polyantha.

Plant:

*Height.*—When plants are cut to a height of 85 cm., flowering stems are produced having a length of approximately 40 to 60 cm. The total plant height when grown in fields at Wasco, Calif., at the end of one growing season is approximately 90 to 100 cm.

*Habit.*—Upright.

Branches:

*Color.*—Young stems: light green, Yellow-Green Group 146C. Adult wood: Medium green, Yellow—Green Group 146B.

*Thorns.*—Size: small. Quantity: very few. Color: pinkish on young stems and greenish on mature wood.

Leaves:

*Stipules.*—Adnate, pectinate, very wide and linear.

*Petioles.*—Upper surface: striped reddish brown on young foliage and medium green on adult foliage with more or less glandular edges. Under surface: light green, smooth, and on rare occasions bears a few prickles.

*Leaflets.*—Number: 3, 5 (most often), and 7. Shape: elliptic. Serration: simple, regular, and well defined. Texture: consistent. General appearance: fairly dense, semi-dull foliage. Color (young foliage): upper surface: dark green, Yellow—Green Group 147A, and more or less stained with reddish coloration. under surface: greyish green, Greyed-Green Group 191A. Color (adult foliage): upper surface: dark green, Yellow—Green Group 147A. under surface: greyish green, Greyed-Green Group 191A.

Inflorescence:

*Number of flowers.*—Commonly multiflowering, approximately 1 to 9 blooms per stem.

*Peduncle.*—Straight, rigid, light green and glandular. The length is approximately 6 to 10 cm. on average.

*Sepals.*—Upper surface: tomentose, greenish in coloration. Under surface: light green, with the outer sepals being more or less glandular and fairly appendiculated.

*Buds.*—Shape: conical. Length: approximately 2 to 2.5 cm. on average. Size: medium. Color upon opening: upper surface: bright red, Red Group 45B. under surface: Red Group 45A.

*Flower.*—Shape: cup-like with parallel sides, semi-double. diameter: approximately 6 cm. on average. Color (when opening begins): upper surface: bright red, Red Group 45B. under surface: Red Group 45A. Color (when blooming): upper surface: bright red, Red Group 45B. under surface: Red Group 45A. Color (at end of opening): upper surface: lighter red, Red Group 45C. under surface: lighter red, Red Group 45C. Fragrance: none. Lasting quality: long lasting (i.e., approximately 7 to 9 days) when cut and placed in a vase. Petal shape: rounded with somewhat notched tips. Petal number: approximately 21 on average. Texture: consistent. Petal drop: good. Stamen number: approximately 56 on average. Anthers: normal, and ochre in coloration. Filaments: light fuschia in coloration, and of irregular heights. Pistils: approximately 33 on average. Stigmas: normal, and yellowish in coloration. Styles: fuschia in coloration, tomentose near the base, more or less twisted, and of irregular heights. Receptacle: medium green in coloration, fairly smooth, and in longitudinal section it is in the shape of a narrow funnel.

Developement:

*Vegetation.*—Strong.

*Blooming.*—Abundant.

*Resistance to disease.*—Good.

*Aptitude to forcing.*—Excellent.

I claim:

1. A new and distinct variety of Polyantha rose plant characterized by the following combination of characteristics:

(a) forms in abundance attractive long lasting semi-double bright red blossoms, (b) exhibits an excellent capacity to be forced in the greenhouse for the production of spray-type fresh flowers, (c) forms vigorous vegetation, (d) exhibits an upright growth habit, and (e) is not particularly affected to cryptogamic diseases;

substantially as herein shown and described.

* * * * *